US 6,747,917 B2

(12) United States Patent
Jennings et al.

(10) Patent No.: US 6,747,917 B2
(45) Date of Patent: Jun. 8, 2004

(54) MENSTRUAL CYCLE MONITOR

(75) Inventors: Victoria H. Jennings, Chevy Chase, MD (US); Marcos Arevalo, Rockville, MD (US)

(73) Assignee: Georgetown University, Washington, DC (US)

( * ) Notice: Subject to any disclaimer, the term of this patent is extended or adjusted under 35 U.S.C. 154(b) by 220 days.

(21) Appl. No.: 10/083,369

(22) Filed: Feb. 27, 2002

(65) Prior Publication Data

US 2003/0144602 A1 Jul. 31, 2003

(51) Int. Cl.⁷ .................... G04B 47/00; G04B 19/00; A61B 10/00; A44C 25/00
(52) U.S. Cl. ................... 368/10; 368/327; 368/223; 600/551; 24/116 A; 63/38; 63/39
(58) Field of Search .............. 368/10, 223, 277–279, 368/327; 24/116 A; 63/38–39; 600/551

(56) References Cited

U.S. PATENT DOCUMENTS

| | | | | | |
|---|---|---|---|---|---|
| 1,661,877 | A | * | 3/1928 | Costello | 235/123 |
| 2,343,592 | A | * | 3/1944 | Tilbrook | 235/78 RC |
| 2,681,545 | A | * | 6/1954 | Hall | 59/80 |
| 3,011,303 | A | * | 12/1961 | Dickinson | 368/28 |
| 3,486,691 | A | * | 12/1969 | Rodriguez | 235/88 R |
| 3,771,716 | A | * | 11/1973 | Sanchez | 235/85 FC |
| 3,964,674 | A | * | 6/1976 | Van der Gaast | 235/88 RC |
| 4,165,709 | A | | 8/1979 | Studer | 116/308 |
| 4,367,527 | A | | 1/1983 | Desjacques | 364/413 |
| 4,770,186 | A | | 9/1988 | Regas et al. | 128/734 |
| 4,915,256 | A | * | 4/1990 | Tump | 221/5 |
| 5,058,084 | A | | 10/1991 | Riesen | 368/10 |
| 5,118,630 | A | | 6/1992 | Glaze | 436/65 |
| 5,477,981 | A | | 12/1995 | Heyl et al. | 221/86 |
| 5,777,905 | A | * | 7/1998 | Dowdle et al. | 708/142 |
| 5,903,524 | A | * | 5/1999 | Clarke | 368/240 |
| 6,022,323 | A | * | 2/2000 | Jackson | 600/551 |
| 6,149,591 | A | | 11/2000 | Henderson et al. | 600/407 |
| 6,545,951 | B1 | | 4/2003 | Lynn | 368/223 |
| 6,585,663 | B1 | * | 7/2003 | Coley et al. | 600/551 |
| 6,600,696 | B1 | * | 7/2003 | Lynn | 368/23 |

FOREIGN PATENT DOCUMENTS

| WO | WO 03/000502 A1 | 1/2003 |
|---|---|---|
| WO | WO 03/070106 A1 | 8/2003 |

OTHER PUBLICATIONS

Letter from Dr. Maria Hengstberger, Aktion Regen to Georgetown, Institute for Reproductive Health concerning "Press release from Jun. 10, 2002, Standard Days Method, CycleBeads," sent by email in Jul., 2002 (2 color pages total).
http://www.aktionregen.at web pages entitled "Geburtenkontrollkette" (6 color pages total).
Http://www.fertilitynecklace.com web pages concerning "Ban Gal Fertility Necklace" (17 color pages total).
http://www.irh.org/news.html web pages entitled "New Natural Method of Family Planning Over 95% Effective in Preventing Pregnancy, Study Finds," dated Jun. 10, 2002 (3 color pages total).

(List continued on next page.)

*Primary Examiner*—Randy W. Gibson
*Assistant Examiner*—Michael L. Lindinger
(74) *Attorney, Agent, or Firm*—Collier Shannon Scott, PLLC (57) ABSTRACT

The invention is related to a menstrual cycle monitor for a human female which includes indicators representing a first day of menstrual bleeding, early infertile days, fertile days, and later infertile days in the menstrual cycle. The indicators together form an ordered set. One indicator of the ordered set is provided with different indicia from indicia provided to other indicators, so as to alert the user of the monitor that she should consult her health care provider if particular circumstances arise. A movable marker also may be provided for indexing with the indicators.

59 Claims, 7 Drawing Sheets

OTHER PUBLICATIONS

Marcos Arévalo et al., "Efficacy of a new method of family planning: the Standard Days Method," *Contraception* 65 (2002): 333–338.

The Standard Days Method: A Modern, Effective Method of Family Planning. Washington: Institute for Reproductive Health, Georgetown University Medical Center, Oct., 2001 (2 pages).

Marianne C. Burkhart et al., "Effectiveness of a Standard–Rule Method of Calendar Rhythm Among Mayan Couples in Guatemala," *International Family Planning Perspectives* 26(3) (2000): 131–136.

Marcos Arevalo et al., "A Fixed Formula to Define the Fertile Window of the Menstrual Cycle as the Basis of a Simple Method of Natural Family Planning," *Contraception* 60 (1999): 357–360.

A. Faúndes et al., Evaluation of the Use of the "Collar" as Natural Method of Family Planning. Final Report. CEMI-CAMP, Nov. of 1997.

A. Faúndes et al., "Simplifying NFP: preliminary report of a pilot study of the 'collar' method in Brazil," *Advances in Contraception* 13 (1997):167–71.

http://www.fhi.org/en/fp/fppubs/network/v17–1/nt1714.html web pages for Sarah Keller, "Traditional Beliefs Part of People's Lives," *Network Fertility Awareness* 17(1) (Fall 1996) (5 color pages total).

V. M. Lamprecht et al., "Development of New Formulas to Identify the Fertile Time of the Menstrual Cycle," *Contraception* 54 (1996): 339–343.

* cited by examiner

MENSTRUAL CYCLE MONITOR

STATEMENT AS TO RIGHTS TO INVENTIONS MADE UNDER FEDERALLY-SPONSORED RESEARCH AND DEVELOPMENT

This invention was made with government support under grant number HRN-A-00-97-000 11-00 from the United States Agency for International Development. The government has certain rights in the invention.

FIELD OF THE INVENTION

The invention is related to an apparatus and method for monitoring a woman's menstrual cycle. More particularly, the invention is related to a mnemonic-based approach for monitoring a woman's menstrual cycle.

BACKGROUND OF THE INVENTION

Worldwide, substantial numbers of women use periodic abstinence as their method of family planning. This method of family planning, generally referred to as the "rhythm method," typically involves recognition of a woman's fertile period using any one of various methods, including a "guess" based on the length of her menstrual cycle. Ovulation may be assumed to occur mid-cycle, and thus the period of abstinence is set accordingly. Unfortunately, although some women have an accurate understanding of their reproductive cycle and thus know when they are most likely to be fertile, many users of periodic abstinence lack such an understanding, thereby preventing them from reliably using period abstinence as a means for preventing pregnancy. In fact, it has been estimated that of the 50 to 60 million women who use periodic abstinence to avoid pregnancy, more than one third have little or no information about their own fertility. Despite the lack of reliability of many rhythm-based techniques, various religious, philosophic, or health considerations nevertheless have led many women to adopt these techniques.

Because knowledge of a woman's reproductive cycle could be used by a woman to assist in determining whether to refrain from or engage in intercourse, depending if conception is desired, various techniques have been developed for tracking the reproductive cycle. For example, some researchers have proposed methods of predicting ovulation that are based on biochemical changes in various body fluids, such as saliva, vaginal secretions, or urine. U.S. Pat. No. 4,770,186 to Regas et al. is directed to a method and apparatus for predicting and detecting the onset of ovulation. The method involves essentially measuring the electrical resistivity of the user's saliva, and by observing peaks and nadirs of changes in the saliva resistivity, ovulation and fertility periods are predicted. The onset of ovulation can be further established by measuring the electrical resistivity of vaginal mucus, which, during the fertile period, shows a nadir on the day immediately preceding ovulation.

In addition, U.S. Pat. No. 6,149,591 to Henderson et al. discloses a device for the in vivo detection of refractive indices of cervical mucus at a female's cervical os. The device detects in vivo physiological changes in a female's cervical mucus, with the changes correlating with the timing of ovulation and thus providing a marker for the fertile period of the menstrual cycle.

U.S. Pat. No. 5,118,630 to Glaze is directed to a method for determining periodic infertility in females. The natural birth control method comprises observance of the first day of menses followed by measurement of urinary progesterone metabolite levels beginning a predetermined number of days after the first day of menses. Urinary progesterone metabolite measurement is performed on days of planned sexual activity until the concentration level exceeds a threshold value indicative of ovulation occurring more than 24 hours previously. Once such a threshold value is observed, the woman may discontinue testing and can consider herself unable to conceive until after the beginning of the subsequent menstrual cycle.

Despite these developments, there exists a need for alternative means for a woman to accurately predict her fertile window. Further, because many women discontinue use of a given apparatus and method, and millions of women do not use any apparatus or method, there exists a need for a simple, inexpensive alternative apparatus and method.

In particular, despite the aforementioned developments, there exists a need for a less intrusive apparatus and method for monitoring a woman's menstrual cycle, based on a "fertile window" during each woman's menstrual cycle when she can become pregnant. In addition, there exists a need for an apparatus and method for helping a woman identify her fertile window to permit informed decisions about whether to avoid intercourse if she does not want to become pregnant. Further, there exists a need for a mnemonic-based apparatus and method for monitoring a woman's menstrual cycle.

SUMMARY OF THE INVENTION

The invention is related to a menstrual cycle monitor for a human female including an initial indicator provided with first indicia representing a first day of menstrual bleeding, a second set of indicators formed by six indicators disposed adjacent one another, each of the six indicators provided with second indicia representing early infertile days, a third set of indicators formed by twelve indicators disposed adjacent one another, each of the twelve indicators provided with third indicia representing fertile days, and a fourth set of indicators formed by thirteen indicators disposed adjacent one another representing later infertile days. The indicators together form an ordered set with the initial indicator disposed adjacent an indicator from the second set, the second set disposed between the initial indicator and the third set, the third set disposed between the second and fourth sets, and an indicator from the fourth set disposed adjacent an indicator from the third set. A twenty-seventh indicator of the ordered set is determined by counting each consecutive indicator starting with the initial indicator, and the twenty-seventh indicator is provided with different indicia from indicia provided to the other indicators in the fourth set.

In some embodiments, the ordered set of indicators are coupled together. Also, the ordered set may include a thirty-second indicator determined by counting each consecutive indicator starting with the initial indicator, with the indicators of the ordered set being coupled together so that the thirty-second indicator is coupled to the initial indicator. In addition, a final indicator may be provided with fifth indicia representing the end of the menstrual cycle, the final indicator being disposed between the initial indicator and thirty-second indicator.

The first, second, third, and fifth indicia may each comprise a shape, and the fifth indicia shape may be different from the first, second, and third indicia shapes. Each indicator may be a bead, and the beads may be coupled together to form a loop. The beads may be tear-drop shaped. In another embodiment, the ordered set may be disposed in an open-ended linear form.

The menstrual cycle monitor also may include a movable marker for placement around and/or coupling to an indicator. A resilient band, sized to fit snugly around an indicator, may serve as the movable marker. The movable marker may be coupled to the ordered set.

The first, second, and third indicia may be different colors. In some embodiments, the indicia of the twenty-seventh indicator may be a first color, the indicia of the other indicators in the fourth set may be a second color, and the first color may be different from the second color. The indicators of the fourth set may be provided with luminescent indicia. Further, the indicia of the twenty-seventh indicator may be a first shape and the indicia of the other indicators in the fourth set may be a second shape, with the first shape being different from the second shape. The indicia of the indicators in the fourth set other than the twenty-seventh indicator may be the same as the second indicia. Also, the second indicia and the indicia of the indicators in the fourth set other than the twenty-seventh indicator may be the same color. The indicia provided to the indicators in the fourth set may also comprise shape and color.

The menstrual cycle monitor may further include a foldable case having an inner portion, a first annular region with a marker disposed thereon, and a second annular region with the ordered set disposed thereon. The first and second annular regions may be coupled to the inner portion of the foldable case and concentric about a central axis. At least one of the first and second annular regions may be rotatable with respect to the other, and the indicators of the ordered set may be indexed with the marker so that the marker is alignable with each indicator.

In some embodiments, a third annular region with date indicia representing days of the week may be included, with the third annular region being concentric about the central axis. The date indicia may be all the days of the week for five weeks, wherein the days of the five weeks begin with a Sunday, end with a Saturday, and are listed consecutively in order of occurrence in a week. The date indicia may be indexed with the indicators of the ordered set so that the date indicia are alignable with each indicator.

The second annular region may be fixed with respect to the foldable case, and the first and third annular regions may be independently rotatable with respect to the second annular region. The first annular region may have an inner diameter and the second annular region may have an outer diameter, with the outer diameter being about the same as or smaller than the inner diameter so that the first annular region is rotatable about an edge of the second annular region defined at the outer diameter. In addition, the second annular region may have an inner diameter and the third annular region may have an outer diameter, with the outer diameter being about the same as or smaller than the inner diameter so that the third annular region is rotatable about an edge of the second annular region defined at the inner diameter.

The date indicia may be indexed with the indicators of the ordered set so that the date indicia are alignable with each indicator at rotatable indexed positions, and the first and third annular regions may be releasably lockable in the rotatable indexed positions. At least two of the first, second, and third annular regions may be disposed at different heights. In some embodiments, the ordered set is disposed clockwise on the second annular region beginning with the initial indicator.

The marker may be an arrow and the indicators of the ordered set may be dots. The first indicia may be a first color, the second indicia may be a second color, and the third indicia may be a third color, with the first, second, and third colors being different from each other. Also, the indicia of the twenty-seventh indicator may be a fourth color, and the indicia of the other indicators in the fourth set may be the second color, with the fourth color being different from the second color.

The menstrual cycle monitor may include a first region with a marker disposed thereon, and a second region with the ordered set disposed thereon. At least one of the first and second regions may be annular and rotatable with respect to the other, and the indicators of the ordered set may be indexed with the marker so that the marker is alignable with each indicator at rotatable indexed positions. The first and second regions may be annular and concentric about a central axis and may be generally disposed in the same plane. Furthermore, the menstrual cycle monitor may include a central display region for indicating time and/or a watch band or bracelet.

The at least one of the first and second regions may be unidirectionally rotatable in clockwise or counterclockwise fashion and releasably lockable in the rotatable indexed positions. The first region may have an inner diameter and the second region may have an outer diameter, the outer diameter being about the same as or smaller than the inner diameter so that the first region is rotatable about an edge of the second region defined at the outer diameter. A central display region may be included for indicating time, with the second region being fixed in location with respect to the central display region. At least one of the first and second regions may be manually rotatable with respect to the other. In some embodiments, at least one of the first and second regions is automatically rotatable with respect to the other.

The ordered set of indicators of the menstrual cycle monitor may be displayed electronically, and the marker may be displayed electronically as well. The ordered set may be graphically displayed on a computer monitor, the screen of a hand-held computer, or displayed via internet communications.

The invention also relates to a method of monitoring the menstrual cycle of a human female including: providing an initial indicator with first indicia representing a first day of menstrual bleeding; providing a second set of indicators comprising six indicators disposed adjacent one another, each of the six indicators provided with second indicia representing early infertile days; providing a third set of indicators comprising twelve indicators disposed adjacent one another, each of the twelve indicators provided with third indicia representing fertile days; providing a fourth set of indicators comprising thirteen indicators disposed adjacent one another representing later infertile days; ordering the indicators together to form an ordered set with the initial indicator disposed adjacent an indicator from the second set, the second set disposed between the initial indicator and the third set, the third set disposed between the second and fourth sets, and an indicator from the fourth set disposed adjacent an indicator from the third set, with the ordered set including a twenty-seventh indicator determined by counting each consecutive indicator starting with the initial indicator; providing the twenty-seventh indicator with different indicia from indicia provided to the other indicators in the fourth set.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

It is known from biological evidence that each woman has a "fertile window" during her menstrual cycle when she can become pregnant. The fertile window includes the 5 days preceding ovulation and the day of ovulation. The window is related to the life span of the sperm, which only survives in the woman's reproductive tract for approximately 5 days, as well as the fact that the egg lives only for about 24 hours.

It is also known that the probability of pregnancy increases from 4% five days before ovulation, to almost 30% just before ovulation, to about 8% on the day of ovulation, and finally to about zero for the remainder of the cycle. See, e.g., A. J. Wilcox, C. R. Weinberg, and D. D. Baird, "Post-ovulatory ageing of the human oocyte and embryo failure," *Human Reproduction* 13(2): 394–97 (1988).

A study of the use of a mnemonic device to assist women in monitoring their cycles was undertaken. A total of 478 women were admitted to the study, the women ranging in age from 18–39 and living in Bolivia, Peru, and the Philippines. Each woman in the study had a self-reported recent history of cycles between 26 and 32 days, and desired to delay pregnancy at least one year. To assist women in monitoring their cycles, each woman was provided with a string of thirty-two beads in which each bead represented a day of the menstrual cycle. The string had a first red bead to represent the first day of menses, followed by six brown beads representing the additional non-fertile days preceding the fertile window, followed by twelve white beads representing fertile days, followed by an additional thirteen brown beads representing non-fertile days. The string of beads also included a moveable, tight-fitting rubber ring, and women were instructed to move the ring onto the red bead on the day their menses began, and to continue moving the ring one bead per day until their menses returned.

In the study, the women were told not to have unprotected intercourse on days the ring was on the white bead, in order to avoid pregnancy. Also, women were told that if menstrual bleeding occurred prior to day 27 of the cycle, or if menstrual bleeding did not occur by the day after they completed all 32 beads, they should seek further assessment and advice from a provider. Women who experienced two cycles outside the 26–32 day range during the study period were advised to use another method, and were removed from the study. In addition, women were asked to continue use of the string of beads for 13 complete cycles.

The results of the study indicated that use of the string of beads provided significant protection from unplanned pregnancy. A cumulative probability of pregnancy of 4.75% over 13 cycles of correct use of the method, and an 11.96% probability of pregnancy under typical use, were indicated by a single decrement multi-censoring life table analysis of the data. Further details can be found in the following publication, which is hereby incorporated by reference in its entirety: Marcos Arévalo, Victoria Jennings, and Irit Sinai, "Efficacy of a new method of family planning: the Standard Days Method," *Contraception* 65(5): May, 2002.

Figure 1:
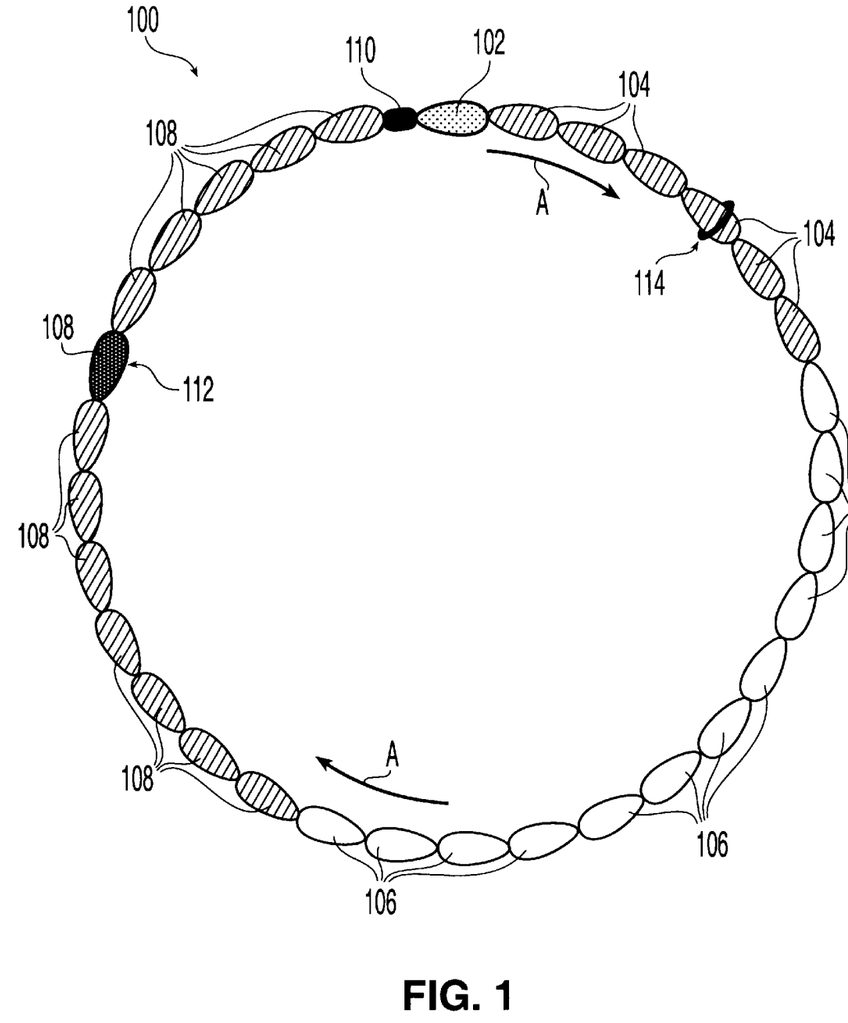
FIG. 1 shows a plan view of a first exemplary embodiment of the present invention as a string of beads such as a loop in a closed arcuate form.

Now, referring to FIG. 1, there is shown a first exemplary embodiment of the present invention as a string of beads such as a loop in a closed arcuate form. Necklace or loop 100 includes thirty-two beads that are strung together in the following order: one bead 102 of a first color representing the first day of menstrual bleeding, six beads 104 of a second color representing the early infertile days, twelve beads 106 of a third color representing fertile days, and thirteen beads 108 of the second color representing the later infertile days. A thirty-third bead 110, preferably smaller than the first thirty-two beads, optionally may be provided to signify the end of the menstrual cycle. The order of the beads is shown graphically by arrow A.

Loop 100 also includes a strong, flexible ring or "band" 114, which may be similar to an o-ring. Ring 114 preferably is sized to fit snugly on a portion of beads 102, 104, 106, 108, but can be moved from one bead to the next to serve as a position marker. Also, ring 114 preferably is formed of rubber or another durable, resilient material. To assist in positioning ring 114 on a bead 102, 104, 106, 108, each bead maybe provided with a circumferential, protruding rib against which ring 114 bears, or a groove in which ring 114 seats.

Figure 1A:
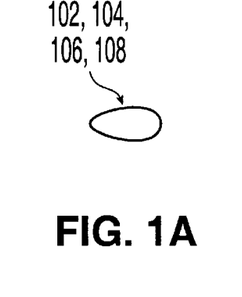
FIG. 1A shows a side view of a bead with a tear-drop shape for use with the present invention.
Figure 1B:
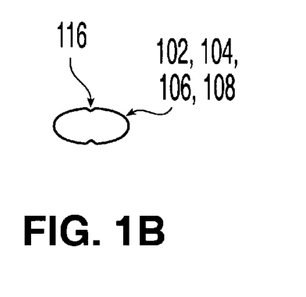
FIG. 1B shows a side view of a bead with a groove for use with the present invention.

Preferably, beads 102, 104, 106, 108, 110 are strung on a strong, durable string, cord or wire that can be securely tied. Loop 100 is knotted or fastened securely to prevent tampering, such that the beads cannot be removed and the order of the beads is preserved. Preferably, bead 110 surrounds the knot or other fastening. One preferred shape for beads 102, 104, 106, 108 is a tear-drop shape, as shown in FIG. 1A, with one end smaller than the other. Preferably, ring 114 is sized to fit snugly on the widest portion of the tear-drop shape. Alternatively, a round or oval shape may be used for beads 102, 104, 106, 108, as shown in FIG. 1B, with a slight indentation or groove 116, such as in the middle. Rings for use with beads having a groove 116 preferably are sized to fit snugly in groove 116. Regardless of the shape, it is preferable that ring 114 fit securely on each bead 102, 104, 106, 108. Preferably, beads 102, 104, 106, 108, 110 are suitably sized to serve as a necklace which could be worn comfortably around a woman's neck or stored in a wallet-sized pouch.

In one embodiment, bead 102 is red to represent a woman's first day of bleeding, while beads 104, 108 are another color such as brown. Beads 106 may be white, for example, and bead 110 may be black. In one exemplary preferred embodiment, beads 106 are luminescent and glow in the dark, so that a woman may visually determine, in the dark, whether ring 114 is located on a bead which indicates a period of fertility, e.g., a period during which unprotected intercourse should be avoided. The contrast of a non-luminescent ring 114 with luminescent beads 106 may be easily discerned in the dark. In an alternate embodiment, ring 114 may be luminescent. In an exemplary preferred embodiment, starting with bead 102 and counting all beads regardless of color in the direction of arrow A, the 27th bead, indicated by bead 112, is provided in a fourth color that is a different color than the other infertile day beads 112 having the second color. Preferably, the fourth color is a slightly different color than the second color, such as a lighter or darker shade of brown. In an alternative embodiment, an indelible mark or cut may be provided instead of, or in addition to, the fourth color on the 27th bead. Preferably, beads 102, 104, 106, 108 are the same size and shape.

When loop 100 is used, ring 114 is initially placed on bead 102 when the first day of menstrual bleeding occurs. Each day, the user moves ring 114 over another bead in the direction of arrow A. Women who do not desire to become pregnant may be counseled to avoid unprotected intercourse when ring 114 is located on any of beads 106. It will be appreciated that while loop 100 is shown with beads 102, 104, 106, 108, and 110 in the order described above for clockwise movement of ring 114 in the direction of arrow A, the beads on loop 100 may be positioned for counterclockwise movement, so long as the aforementioned order of movement of ring 114 successively on beads 102, 104, 106, 108, and 110 is preserved during the cycle.

Loop 100 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by bead 112, this bead 112 serves as a marker to alert the woman about the need to see her health care provider for further investigation. In such a case, loop 100 may not be appropriate for tracking the menstrual cycle of the user. In particular, while women who only occasionally have menstrual cycles longer than 32 days or shorter than 26 days may still rely on loop 100, this apparatus is less predictive of menstrual cycles for women who consistently have cycles outside the 26 to 32 day range.

In an alternative embodiment, beads 102, 104, 106, 108 of loop 100 may be consecutively numbered from one through thirty-two, thus providing indicia other than color for indicating place in the cycle.

Loop 100 permits a woman to improve her understanding of her reproductive cycle. Advantageously, loop 100 may serve as a support tool for partner communication, helping a woman's partner to become more involved in family planning. It also may be used as a teaching tool for young women shortly after reaching puberty. While the loop may be worn by an individual around her neck, it preferably is small enough to be stored in a small purse to permit privacy. Other advantages of the present invention include the ease of teaching, learning, and using the device and method, the lack of side effects, and the lack of interference with future fertility.

Loop 100 may be produced at low-cost, using lightweight polymer beads that may be readily available from commercial sources. Also, the basic design premises of loop 100 facilitate its manufacture in localities worldwide; if the preferred shapes of beads are not locally available, other shapes can be used without departing from the present invention, as long as a marker such as a ring is provided which can be moved from one bead to the next while remaining secure on the intended bead.

Figure 2:
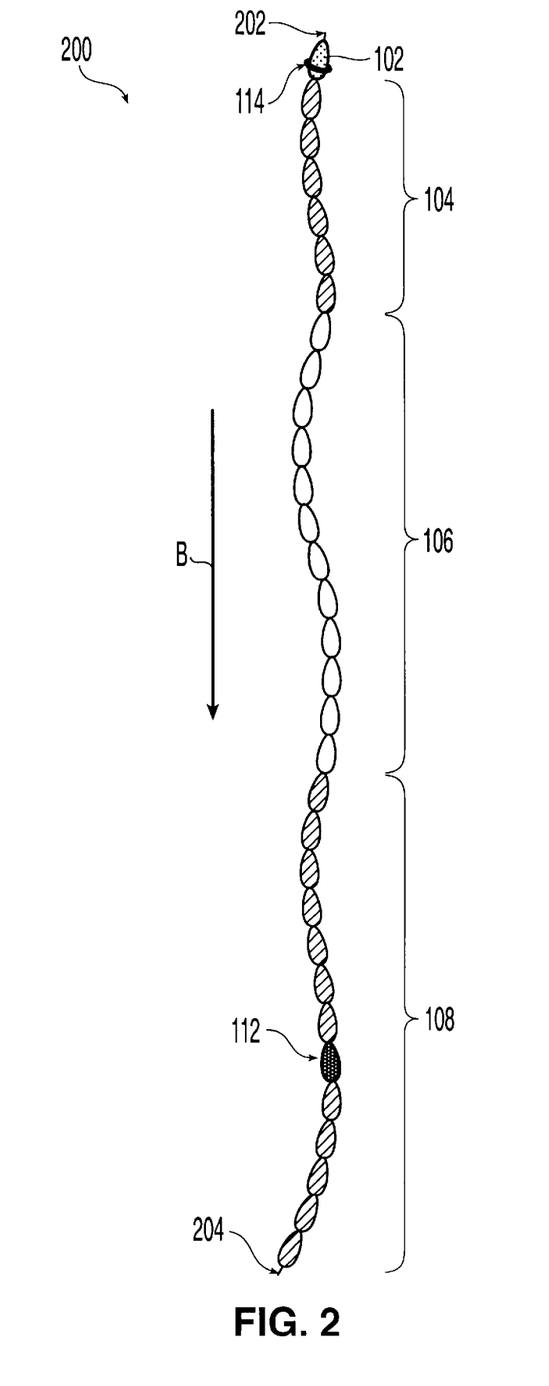
FIG. 2 shows a plan view of a second exemplary embodiment of the present invention as a string of beads in an open-ended linear form.

Turning to FIG. 2, a second exemplary embodiment of the present invention is shown as a string of beads in an open-ended linear form. Chain 200 includes thirty-two beads that are strung together in the following order: one bead 102 of a first color representing the first day of menstrual bleeding, six beads 104 of a second color representing the early infertile days, twelve beads 106 of a third color representing fertile days, and thirteen beads 108 of the second color representing the later infertile days. The order of the beads is shown graphically by arrow B. Chain 200 also includes a strong, flexible ring or "band" 114, as described above with respect to loop 100. Preferably, beads 102, 104, 106, 108 are strung on a strong, durable string, cord or wire that can be securely knotted or otherwise fastened at both ends 202, 204 to prevent tampering, such that the beads cannot be removed from chain 200 and the order of the beads is preserved. In an exemplary preferred embodiment, starting with bead 102 and counting all beads regardless of color in the direction of arrow A, the 27th bead, indicated by bead 112, is provided in a fourth color that is a different color than the other infertile day beads 112 having the second color. The preferred and alternate shapes, colors and/or other indicia, and other features of beads 102, 104, 106, 108, including bead 112, as described above for loop 100 are also applicable to chain 200.

When chain 200 is used, ring 114 is initially placed on bead 102 when the first day of menstrual bleeding occurs. Each day, the user moves ring 114 over another bead in the direction of arrow B. Women who do not desire to become pregnant may be counseled to avoid unprotected intercourse when ring 114 is located on any of beads 106. It will be appreciated that while chain 200 is shown with beads 102, 104, 106, 108, and 110 in the order described above for downward movement of ring 114 in the direction of arrow B, the beads on chain 200 may be positioned in any orientation that permits movement of ring 114 successively on beads 102, 104, 106, 108, and 110 during the cycle.

As with loop 100, chain 200 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by bead 112, this bead 112 serves as a marker to alert the woman about the need to see her health care provider for further investigation. In such a case, chain 200 may not be appropriate for tracking the menstrual cycle of the user. On the day after the woman moves ring 114 to the final bead 204, she removes ring 114 from final bead at end 204 and re-places it at end 202 at the first position, bead 102, at the beginning of the next cycle.

Figure 3:
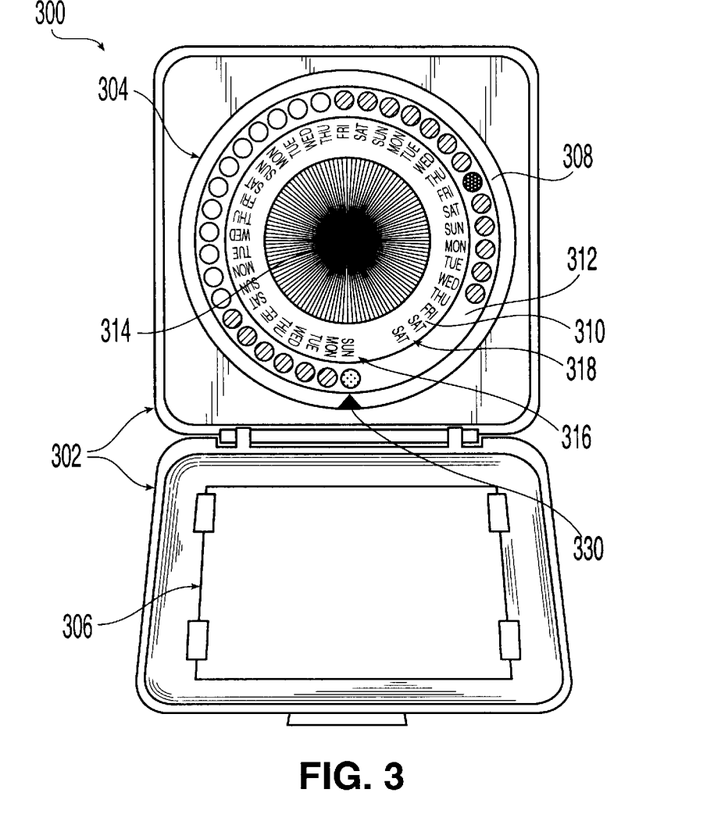
FIG. 3 shows front perspective view of a third exemplary embodiment of the present invention in the form of a compact.

With reference to FIG. 3, a third exemplary embodiment of the present invention is shown in the form of a compact 300, which includes a foldable case 302, an indicator region 304, and optionally a region 306 suitable for storing or otherwise displaying directions for usage. Preferably, region 304 includes an outer annular region 308, an inner annular region 310, and an intermediate annular region 312 disposed between regions 308, 310. In the preferred embodiment, regions 308, 310, 312 are concentric about a central axis 314. In one embodiment, as shown, inner annular region 310 is provided with the days of the week in order beginning with Sunday and ending with Saturday. The seven days are repeated in the same order five times. Thus, the cycle runs clockwise from Sunday at initial position 316 to Saturday at final position 318. Preferably, each of outer annular region 308 and inner annular region 310 is moveable, independent of one another, and may be rotated and releasably locked to a desired position as will be described. Intermediate annular region 312 preferably is fixed in position.

Figure 3A:
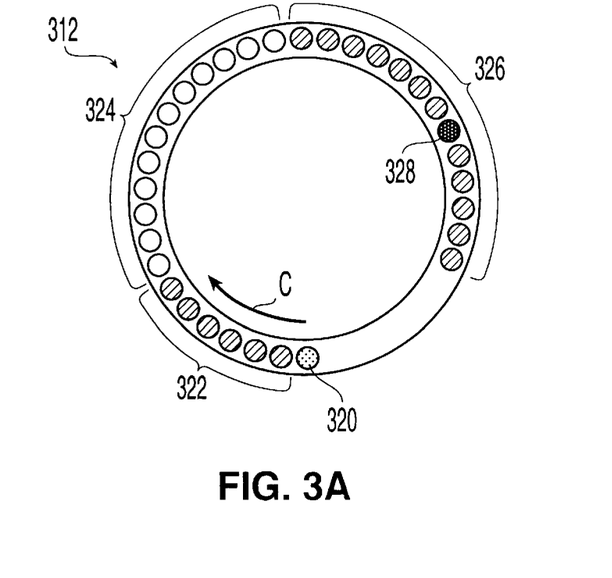
FIG. 3A shows a top view of the intermediate annular region of the compact of FIG. 3.

Intermediate annular region 312 is provided with thirty-two indicators such as color-coded dots. The indicators are provided in the following order, as shown in FIG. 3A: one indicator 320 of a first color representing the first day of menstrual bleeding, six indicators 322 of a second color representing the early infertile days, twelve indicators 324 of a third color representing fertile days, and thirteen indicators 326 of the second color representing the later infertile days. The order of the indicators is shown graphically by arrow C. In an exemplary preferred embodiment, starting with indicator 320 and counting all indicators regardless of color in the direction of arrow C, the 27th indicator, indicated by indicator 328, is provided in a fourth color that is a different color than the other infertile day indicators 326 having the second color. Alternate shapes, colors and/or other indicia, and other features of indicators 320, 322, 324, 326, including indicator 328, as described for example above for loop 100, may also be applied to compact 300. In addition, indicators 320, 322, 324, 326, including indicator 328, may be provided as depressions or protrusions.

Outer annular region 308 is provided with a marker 330, such as an arrow. Marker 330 serves a similar purpose to that described above with respect to ring 114.

Preferably, the days of the week on inner annular region 310, the indicators on intermediate annular region 312, and the arrow on outer annular region 308 may be aligned with respect to each other, as shown with the general indexing depicted in FIG. 3.

When compact 300 is used, inner annular region 310 is initially moved, once per cycle, to align the day of the week closest to initial position 316 with indicator 320, representing the start of menses. Each day, the user rotates outer annular region 308 in the direction of arrow C, so that marker 330 is aligned with the next indicator in the series. Women who do not desire to become pregnant may be counseled to avoid unprotected intercourse when marker 330 is aligned with any of indicators 324. It will be appreciated that while compact 300 is shown with indicators 320, 322, 324, 326 in the order described above for counterclockwise movement of marker 330 in the direction of arrow C, the indicators on compact 300 may be positioned for clockwise movement, so long as the aforementioned order of movement of marker 330 for successive alignment with indicators 320, 322, 324, 326 is preserved during the cycle.

As discussed above with respect to loop 100 and chain 200, compact 300 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by indicator 328, this indicator 328 serves to alert the woman about the need to see her health care provider for further investigation. In such a case, compact 300 may not be appropriate for tracking the menstrual cycle of the user.

Preferably, compact 300 may be fabricated from virtually any durable material, but in the preferred embodiment of the present invention, components of compact 300 such as foldable case 302 are fabricated from a polymeric material by injection molding. Preferably, compact 300 is lightweight and sized to fit in a woman's pocketbook.

Any of a wide variety of mechanisms may be used to permit each of outer annular region 308 and inner annular region 310 to be releasably locked to a desired rotational position, and to permit indexing of the days of the week on inner annular region 310, the indicators on intermediate annular region 312, and the arrow on outer annular region 308 with respect to each other. For example, compact 300 may incorporate separate mechanisms to permit rotation of regions 308, 310, respectively, such as the mechanism used with the twist article dispenser shown and described in U.S. Pat. No. 5,477,981 to Heyl et al., the entire content of which is expressly incorporated herein by reference thereto. In one exemplary preferred embodiment, outer annular region 308 and inner annular region 310 of compact 300 may each be spring loaded, so that downward pressure on a region 308, 310 releases the locked position of the region and permits rotation. Further, in some embodiments, rotation may only be permitted in one direction, for example, to permit marker 330 to be successively aligned with indicators 320, 322, 324, 326 during the course of the cycle. Once rotation to the next position has been effected, downward pressure on the region 308, 310 is released and the region is resiliently biased upward by the spring into a locked position.

Figure 3B:
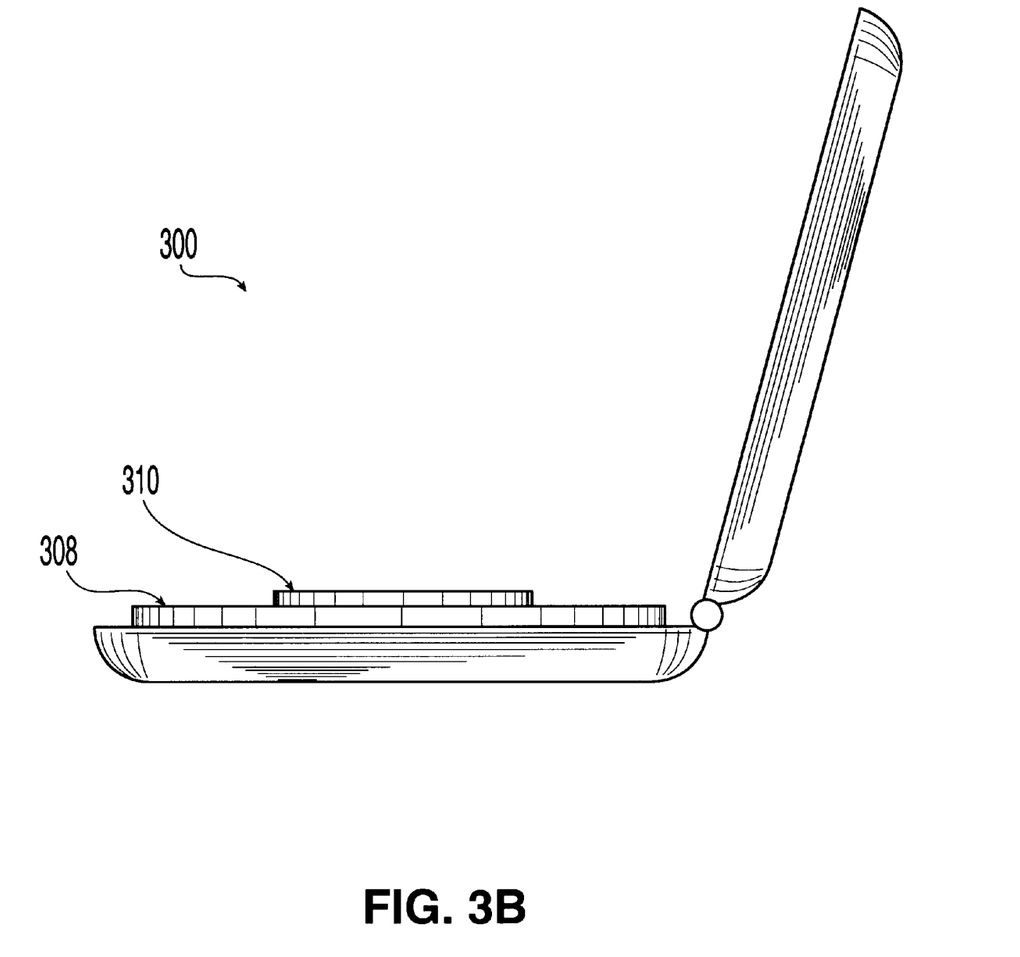
FIG. 3B shows a side view of the compact of FIG. 3.

In one preferred embodiment of compact 300, outer annular region 308 and inner annular region 310 are provided at different heights in their locked rotational positions. As shown for example in FIG. 3B, region 310 may protrude above region 308. Alternatively, region 308 may protrude above region 310. Optionally, intermediate annular region may be provided at the same height as a region 308, 310, or at a different height.

In an alternative embodiment of compact 300, only outer annular region 308 and intermediate annular region 312 are provided. Inner annular region 310 is not used.

Figure 4:
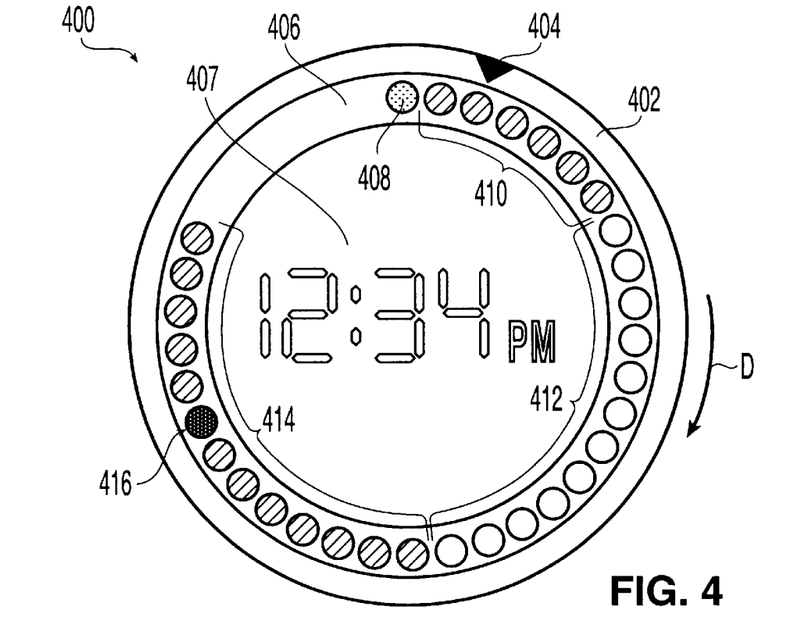
FIG. 4 shows a plan view of another exemplary embodiment of the present invention in the form of a dial-based cycle indication system that is integrated with a watch.

Referring next to FIG. 4, another exemplary embodiment of the present invention is shown in the form of a dial-based cycle indication system that is integrated with a watch, similar to a diver's watch or airplane pilot's watch. System 400 includes an outer, unidirectionally rotatable, annular turning bezel 402 with a marker 404, such as an arrow. An inner annular region 406 is also provided, preferably fixed in location with respect to central display region 407, and region 406 includes thirty-two indicators such as color-coded dots. The indicators are provided in the following order, as shown in FIG. 4: one indicator 408 of a first color representing the first day of menstrual bleeding, six indicators 410 of a second color representing the early infertile days, twelve indicators 412 of a third color representing fertile days, and thirteen indicators 414 of the second color representing the later infertile days. The order of the indicators is shown graphically by arrow D, which also shows the preferred clockwise rotation of turning bezel 402. In an exemplary preferred embodiment, starting with indicator 408 and counting all indicators regardless of color in the direction of arrow D, the 27th indicator, indicated by indicator 416, is provided in a fourth color that is a different color than the other infertile day indicators 414 having the second color. Alternate shapes, colors and/or other indicia, and other features of indicators 408, 410, 412, 414, including indicator 416, as described for example herein, may also be applied to system 400. As discussed above the movable marker and/or those indicators which indicate fertile days may be luminescent so that the alignment may be seen in the dark.

When system 400 is used, the user manually rotates bezel 402 so that marker 404 is aligned with indicator 408, representing the start of menses. Marker 404 is indexed with indicators 408, 410, 412, 414, and each day, the user rotates bezel 402 in the direction of arrow D, so that marker 404 is aligned with the next indicator in the series. Women who do not desire to become pregnant may be counseled to avoid unprotected intercourse when marker 404 is aligned with any of indicators 412. It will be appreciated that while system 400 is shown with indicators 408, 410, 412, 414 in the order described above for clockwise movement of marker 404 in the direction of arrow D, bezel 402 may be unidirectionally rotatable in counterclockwise fashion if the indicators on system 400 are suitably disposed, such that the aforementioned order of movement of marker 404 for successive alignment with indicators 408, 410, 412, 414 is preserved during the cycle. Preferably, bezel 402 is releasably lockable at each indexed position.

As discussed above for example with respect to loop 100 and chain 200, system 400 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by indicator 416, this indicator 416 serves to alert the woman about the need to see her health care provider for further investigation. In such a case, system 400 may not be appropriate for tracking the menstrual cycle of the user.

While central display region 407 is shown with digital time indication means, as typically found with a digital watch, time may alternatively or additionally be shown in analog format, such as with hour, minute, and second hands. Preferably, system 400 is lightweight and sized to be worn on a user's wrist, such as by using a suitably attached watch band or bracelet.

While the embodiment of FIG. 4 preferably incorporates a digital watch, it should be appreciated that a central display region 407 is not required. In some embodiments, an outer, unidirectionally rotatable, annular turning bezel 402 with a marker 404, such as an arrow, is coupled to an inner annular region 406 with indicators as described above. The two annular components are indexed, and a user moves the components with respect to each other to indicate the progress of the cycle. In this alternate embodiment, the indicators and markers, respectively, may be located on outer annular turning bezel 402 or inner annular region 406. Such an arrangement, for example, may be sized to be worn on a user's wrist, such as a bracelet. In yet another alternate embodiment, marker 404 may be a separate component such as a needle, instead of a printed arrow.

Figure 4A:
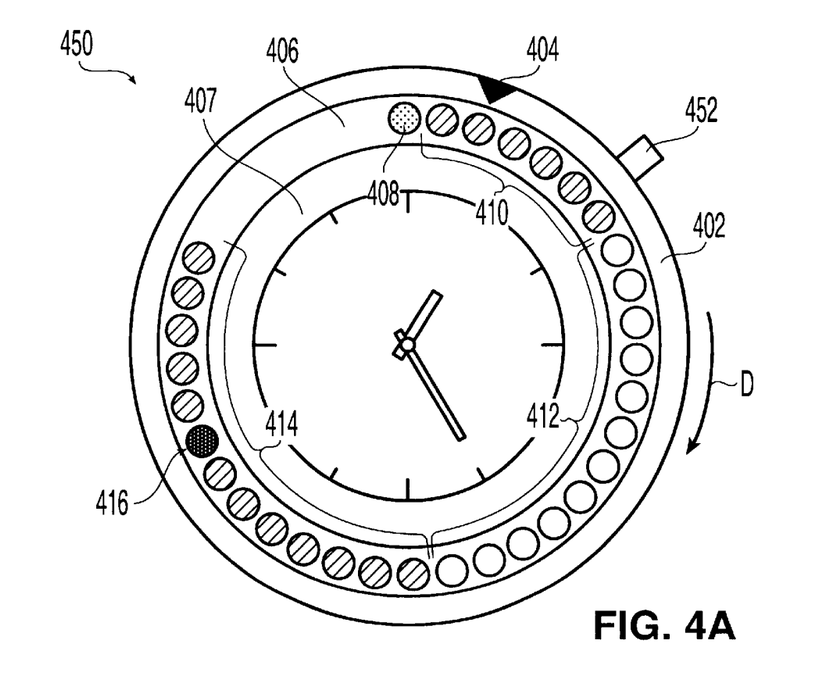
FIG. 4A shows a plan view of yet another exemplary embodiment of the present invention in the form of a dial-based cycle indication system that is integrated with a watch.

An alternate exemplary embodiment of a dial-based cycle indication system that is integrated with a watch is shown in FIG. 4A. System 450 includes an outer, unidirectionally rotatable, annular turning bezel 402 with a marker 404, such as an arrow. An inner annular region 406 is also provided, preferably fixed in location with respect to central display region 407, and region 406 includes thirty-two indicators such as color-coded dots as described above with respect to system 400. In this embodiment, bezel 402 is mechanically rotated about inner annular region 406, so that marker 404 is aligned with indicator 408, representing the start of menses. Such mechanical rotation may be effected, for example, by depressing a button 452 which resets marker 404 to be aligned with indicator 408. Marker 404 is mechanically indexed with indicators 408, 410, 412, 414, and each day, bezel 402 automatically rotates one position in the direction of arrow D, so that marker 404 is aligned with the next indicator in the series. Suitable mechanisms for effecting the automated, mechanical movement, as well as the mechanics of a reset button 452, are well-known in the art of watch making.

While central display region 407 of system 450 is shown with hour, minute, and second hands to display time in analog format, time may alternatively or additionally be displayed in digital format, as typically found with a digital watch. Preferably, system 450 is lightweight and sized to be worn on a user's wrist, such as by using a suitably attached watch band or bracelet.

In another alternative embodiment of a dial-based cycle indication system that is integrated with a watch, the user may reset the position of marker 404, so that marker 404 is aligned with indicator 408 to indicate the start of menses. A winding mechanism, such as typically provided for a wind-up wrist watch, may be manually used to provide the needed energy to permit marker 404 to automatically move from one indicator to the next.

Alternate shapes, colors and/or other indicia, and other features of indicators as described for example herein, may also be applied to system 450 and the variants thereof described above.

Figure 5:
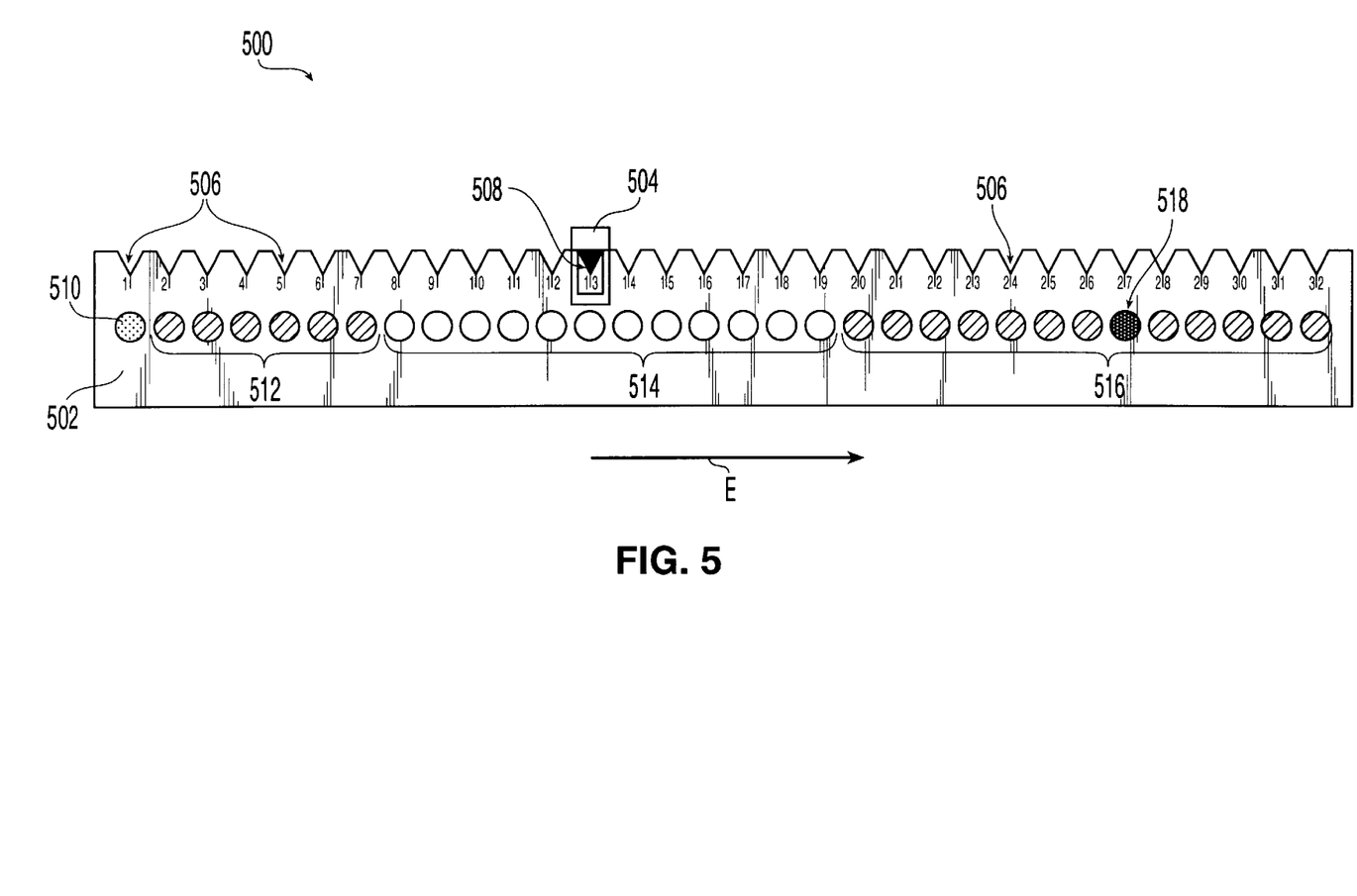
FIG. 5 shows a plan view of another exemplary embodiment of the present invention in the form of a linear based cycle indication system.

Turning next to FIG. 5, another exemplary embodiment of the present invention is shown in the form of a linear based cycle indication system. System 500 includes a scale portion 502 and a discrete, movable marker portion 504. Each position on scale portion 502 is denoted, in part, by a V-shaped groove 506. Marker portion 404 includes a V-shaped protrusion 508 which mates with each groove 506 to rest therein. V-shaped grooves 506 are optionally consecutively numbered on scale portion 502. In addition, scale portion 502 preferably is provided with thirty-two indicators such as color-coded dots, which are indexed to the V-shaped grooves 506. The indicators are provided in the following order, as shown in FIG. 5: one indicator 510 of a first color representing the first day of menstrual bleeding, six indicators 512 of a second color representing the early infertile days, twelve indicators 514 of a third color representing fertile days, and thirteen indicators 516 of the second color representing the later infertile days.

The order of the indicators is shown graphically by arrow E, which also shows the preferred left-to-right movement of marker portion 504. In an exemplary preferred embodiment, starting with indicator 510 and counting all indicators regardless of color in the direction of arrow E, the 27th indicator, indicated by indicator 518, is provided in a fourth color that is a different color than the other infertile day indicators 516 having the second color. Alternate shapes, colors and/or other indicia, and other features of indicators 510, 512, 514, 516, including indicator 518, as described for example above for loop 100, may also be applied to system 500. As discussed above the movable marker and/or those indicators which indicate fertile days may be luminescent so that the alignment may be seen in the dark.

When system 500 is used, the user manually moves marker portion 504 so that marker portion 504 is aligned with indicator 510, representing the start of menses. Marker portion 504 is movable to V-shaped grooves 506, which are indexed with indicators 510, 512, 514, 516. Each day, the user moves marker portion 504 in the direction of arrow E, so that marker 504 is aligned with the next indicator in the series. Women who do not desire to become pregnant may be counseled to avoid unprotected intercourse when marker 504 is aligned with any of indicators 514. It will be appreciated that while system 500 is shown with indicators 510, 512, 514, 516 in the order described above for left-to-right movement of marker portion 504 in the direction of arrow E, marker portion 504 alternatively may be moved in right-to-left fashion if the indicators on system 500 are suitably disposed, such that the aforementioned order of movement of marker 504 for successive alignment with indicators 510, 512, 514, 516 is preserved during the cycle. At the start of each cycle on the first day of menses, marker portion 504 is moved to a position aligned with indicator 510.

Again, as discussed above for example with respect to loop 100 and chain 200, system 500 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by indicator 518, this indicator 518 serves to alert the woman about the need to see her health care provider for further investigation. In such a case, system 500 may not be appropriate for tracking the menstrual cycle of the user.

System 500 is similar in operation to movement of an indicator on a mechanical health care balance, used to monitor one's body weight. The similarity renders system 500 adaptable for use with such a personal health care balance. Thus, in some embodiments, system 500 may be mounted on one's personal health care balance, so that during a daily weight check, a woman moves marker 504 to the next position.

Alternate shapes, colors and/or other indicia, and other features of indicators as described for example herein, may also be applied to system 500.

Figure 6:
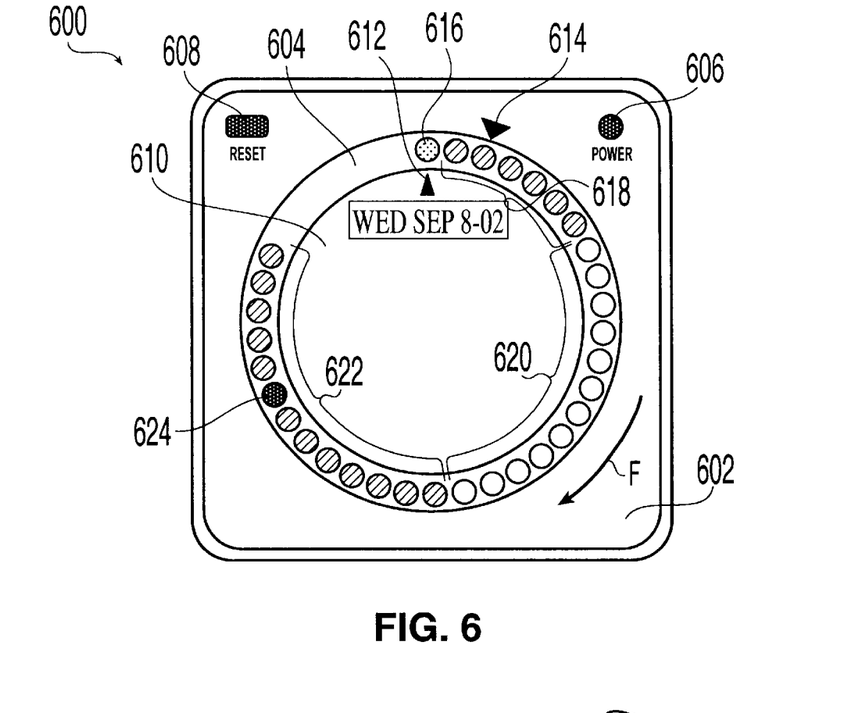
FIG. 6 shows a plan view of another exemplary embodiment of the present invention in the form of an electronic cycle indication system.

With reference next to FIG. 6, another exemplary embodiment of the present invention is shown in the form of an electronic cycle indication system. System 600 includes a housing 602, indicator region 604, power button 606, and reset button 608. A central display region 610 is provided for optional digital display of the date 612 of the first day of menses. Further, a marker 614 such as an arrow is digitally displayed along the outer perimeter of indicator region 604 for indicating the current place in the cycle.

Indicator region 604 includes thirty-two indicators such as color-coded dots, which are fixed in position with respect to housing 602. The indicators are provided in the following order, as shown in FIG. 6: one indicator 616 of a first color representing the first day of menstrual bleeding, six indicators 618 of a second color representing the early infertile days, twelve indicators 620 of a third color representing fertile days, and thirteen indicators 622 of the second color representing the later infertile days. The order of the indicators is shown graphically by arrow F, which also shows the preferred clockwise movement of marker 614. In an exemplary preferred embodiment, starting with indicator 616 and counting all indicators regardless of color in the direction of arrow F, the 27th indicator, indicated by indicator 624, is provided in a fourth color that is a different color than the other infertile day indicators 622 having the second color. Alternate shapes, colors and/or other indicia, and other features of indicators 616, 618, 620, 622, including indicator 624, as described for example above for loop 100, may also be applied to system 600. As discussed above, the movable marker and those indicators which indicate fertile days may be luminescent so that the alignment may be seen in the dark. Although indicator region 604 is shown with indicators 616, 618, 620, 622 aligned in a circular fashion, similar to the annular regions of the embodiments of FIGS. 4 and 4A, in an alternate embodiment indicator region 604 may include indicators 616, 618, 620, 622 disposed in a linear configuration, similar to the configuration shown in FIG. 5. In addition, other alternate embodiments may use other configurations of indicators, for example as described herein.

When system 600 is used, the user depresses the reset button to move marker 614 into alignment with indicator 616, representing the start of menses. At this time, central display region 610 also is reset and displays the new date 612 of the first day of menses. Marker 614 is indexed with indicators 616, 618, 620, 622, and each day, marker 614 automatically rotates in the direction of arrow F, so that marker 614 is aligned with the next indicator in the series. Women who do not desire to become pregnant may be counseled to avoid unprotected intercourse when marker 614 is aligned with any of indicators 620. It will be appreciated that while system 600 is shown with indicators 616, 618, 620, 622 in the order described above for clockwise movement of marker 614 in the direction of arrow F, marker 614 may be displayed in counterclockwise fashion if the indicators on system 600 are suitably disposed, such that the aforementioned order of movement of marker 614 for successive alignment with indicators 616, 618, 620, 622 is preserved during the cycle.

As discussed above with respect to other embodiments of the present invention, system 600 is particularly suitable for use by women whose menstrual cycles last between 26 and 32 days, the fertility window being from day 8 through day 19 of their menstrual cycle. In the event that a woman gets her period prior to the 27th day of her menstrual cycle, indicated by indicator 624, this indicator 624 serves to alert the woman about the need to see her health care provider for further investigation. In such a case, system 600 may not be appropriate for tracking the menstrual cycle of the user.

Figure 7:
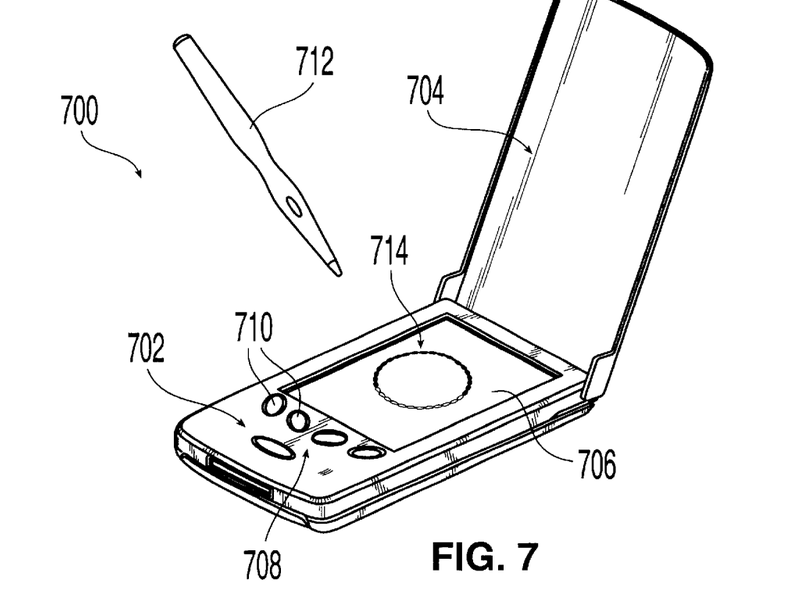
FIG. 7 shows a side perspective view of another exemplary embodiment of the present invention in the form of an electronic cycle indication system provided by a Personal Digital Assistant.

In yet another exemplary embodiment according to the present invention, an electronic cycle indication system is provided by a hand-held computer such as a Personal Digital Assistant (PDA). As shown in FIG. 7, such a electronic cycle indication system 700 includes a hand-held casing 702 and a protective cover 704 pivotally arranged on an end of the casing 702. A touch screen 706 and a switch panel 708 including switch buttons 710 which are connected to an electronic circuit (not shown) are provided on a front side of the casing 702, and may be covered by pivoting the protective cover 704 thereto. A stylus 710 is provided for touching the touch screen 706 to perform data input tasks on PDA indication system 700.

A graphical representation of any menstrual cycle tracking system, as described above, may be shown on touch screen 706. For example, a graphical representation of loop 100 may be shown, for example graphical loop 714, and instead of manually moving a ring 114 from one bead to the next to serve as a position marker, the position marking may be done graphically, for example, by emphasizing a given "bead" or graphically showing a ring 114 disposed on a desired bead 102, 104, 106, 108. Movement of graphical ring 114 may be automated, such that a user need only reset the position of ring 114 on the first day of menses. As above, thirty-two indicators such as color-coded beads, are displayed. The indicators are provided in the following order: one indicator of a first color representing the first day of menstrual bleeding, six indicators of a second color representing the early infertile days, twelve indicators of a third color representing fertile days, and thirteen indicators of the second color representing the later infertile days. In an exemplary preferred embodiment, starting with the first indicator and counting all indicators regardless of color in the described order, the 27th indicator is provided in a fourth color that is a different color than the other infertile day indicators having the second color. Various alternate shapes, sizes, colors, and other indicia may be provided for the display of the indicators, also as described above. PDA indication system 700 is particularly suitable for use by women whose menstrual cycles last between 26 and 32 days, the fertility window being from day 8 through day 19 of their menstrual cycle.

In an additional exemplary embodiment, similar graphical representation of indicators and markers, as described for use with the other embodiments of the present invention, may be accessible, for example, through the internet. One or more computers may be linked together by a computer network, which may include a server, router or the like, and additional computers that permit data, instructions and/or messages to be passed among the networked computers. Mass storage devices may be connected to the server, or to any of the computers, and some of the computers may include an independent network connection between them. The design, construction, and implementation of a computer network suitable for the present invention may be achieved in a multitude of approaches, as known in the art. Regarding the computer networks employed in the present invention, these networks include a set of communications channels interconnecting a set of computer systems that can communicate with each other. Among the many communications channels suitable for use with the present invention are common transmission media such as twisted pair wires, coaxial cable, optical fibers, satellite links, and/or digital microwave radio. However, the present development need not be implemented solely with the aforementioned types of communication channels. Distributed computing systems over wide area networks are contemplated, although local area networks may also be appropriate for some configurations of the present invention. The wide-area and local-area networks may be combined in use, most appropriately in the form of the internet. The internet is contemplated to provide one means upon which to fashion the present invention, although other communication systems as known to those skilled in the art may instead be employed.

Computers may be provided with an input/output source, which is often chosen as a keyboard, mouse, stylus, or other suitable device, and a display device such as a monitor. Furthermore, a network connection may be provided with each computer. Those skilled in the art will also contemplate other configurations of the computers and associated technology, which are readily usable with the present development.

A graphical representation of any menstrual cycle tracking system, as described above, may be shown on the display device. Such a representation and its operation are preferably similar to that described above with respect to PDA indication system 700.

Electronic cycle indication system 700, as well as those embodiments making use of graphical representations of the menstrual cycle monitor of the present invention as displayed on computer monitors and through the use of the internet, are particularly suitable as teaching tools for young women shortly after reaching puberty. The teaching tools may assist in conveying an understanding of the female reproductive cycle, and in particular may assist in conveying an understanding of the "fertile window" during each woman's menstrual cycle when she can become pregnant. The teaching tools, for example, may be used in health education classes.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A menstrual cycle monitor for a human female comprising:
    an initial indicator provided with first indicia representing a first day of menstrual bleeding;
    a second set of indicators comprising six indicators disposed adjacent one another, each of the six indicators provided with second indicia representing early infertile days;
    a third set of indicators comprising twelve indicators disposed adjacent one another, each of the twelve indicators provided with third indicia representing fertile days; and
    a fourth set of indicators disposed adjacent one another representing later infertile days,
    wherein the indicators together comprise an ordered set with the initial indicator disposed adjacent an indicator from the second set, the second set disposed between the initial indicator and the third set, the third set disposed between the second and fourth sets, and an indicator from the fourth set disposed adjacent an indicator from the third set, and
    the ordered set includes a twenty-seventh indicator determined by counting each consecutive indicator starting with the initial indicator, and the twenty-seventh indicator is provided with different indicia from indicia provided to the other indicators in the fourth set.

2. The menstrual cycle monitor of claim 1, wherein the ordered set of indicators are coupled together.

3. The menstrual cycle monitor of claim 1, wherein the ordered set includes a thirty-second indicator determined by counting each consecutive indicator starting with the initial indicator, the indicators of the ordered set being coupled together with the thirty-second indicator being coupled to the initial indicator.

4. The menstrual cycle monitor of claim 3, further comprising a final indicator provided with fifth indicia representing the end of the menstrual cycle, the final indicator being disposed between the initial indicator and thirty-second indicator.

5. The menstrual cycle monitor of claim 4, wherein the first, second, third, and fifth indicia each comprise a shape, and the fifth indicia shape is different from the first, second, and third indicia shapes.

6. The menstrual cycle monitor of claim 4, wherein each indicator comprises a bead, and the beads are coupled together to form a loop.

7. The menstrual cycle monitor of claim 2, wherein each indicator comprises a bead, and the beads are coupled together to form a loop.

8. The menstrual cycle monitor of claim 7, wherein the beads are tear-drop shaped.

9. The menstrual cycle monitor of claim 3, further comprising a movable marker for placement around an indicator.

10. The menstrual cycle monitor of claim 9, wherein the movable marker comprises a resilient band sized to fit snugly around an indicator.

11. The menstrual cycle monitor of claim 9, wherein the movable marker is coupled to the ordered set.

12. The menstrual cycle monitor of claim 1, wherein the first, second, and third indicia comprise different colors.

13. The menstrual cycle monitor of claim 1, wherein the indicia of the twenty-seventh indicator comprises a first shape, the indicia of the other indicators in the fourth set comprises a second shape, and the first shape is different from the second shape.

14. The menstrual cycle monitor of claim 1, wherein the indicia of the twenty-seventh indicator comprises a first color, the indicia of the other indicators in the fourth set comprises a second color, and the first color is different from the second color.

15. The menstrual cycle monitor of claim 1, further comprising a movable marker for coupling to an indicator.

16. The menstrual cycle monitor of claim 1, wherein the indicators of the fourth set are provided with luminescent indicia.

17. The menstrual cycle monitor of claim 1, wherein the indicia of the indicators in the fourth set other than the twenty-seventh indicator is the same as the second indicia.

18. The menstrual cycle monitor of claim 1, wherein the second indicia and the indicia of the indicators in the fourth set other than the twenty-seventh indicator comprise the same color.

19. The menstrual cycle monitor of claim 1, wherein the ordered set is disposed in an open-ended linear form.

20. The menstrual cycle monitor of claim 1, further comprising:
a foldable case having an inner portion;
a first annular region with a marker disposed thereon; and
a second annular region with the ordered set disposed thereon,
wherein the first and second annular regions coupled to the inner portion of the foldable case and concentric about a central axis, at least one of the first and second annular regions is rotatable with respect to the other, and the indicators of the ordered set are indexed with the marker so that the marker is alignable with each indicator.

21. The menstrual cycle monitor of claim 20, further comprising a third annular region with date indicia representing days of the week, the third annular region being concentric about the central axis.

22. The menstrual cycle monitor of claim 21, wherein the date indicia comprises all the days of the week for five weeks.

23. The menstrual cycle monitor of claim 22, wherein the days of the five weeks begin with a Sunday, end with a Saturday, and are listed consecutively in order of occurrence in a week.

24. The menstrual cycle monitor of claim 23, wherein the date indicia are indexed with the indicators of the ordered set so that the date indicia are alignable with each indicator.

25. The menstrual cycle monitor of claim 21, wherein the second annular region is fixed with respect to the foldable case, and the first and third annular regions are independently rotatable with respect to the second annular region.

26. The menstrual cycle monitor of claim 21, wherein the first annular region has an inner diameter and the second annular region has an outer diameter, the outer diameter being about the same as or smaller than the inner diameter so that the first annular region is rotatable about an edge of the second annular region defined at the outer diameter.

27. The menstrual cycle monitor of claim 21, wherein the second annular region has an inner diameter and the third annular region has an outer diameter, the outer diameter being about the same as or smaller than the inner diameter so that the third annular region is rotatable about an edge of the second annular region defined at the inner diameter.

28. The menstrual cycle monitor of claim 21, wherein:
the date indicia are indexed with the indicators of the ordered set so that the date indicia are alignable with each indicator at rotatable indexed positions, and
the first and third annular regions are releasably lockable in the rotatable indexed positions.

29. The menstrual cycle monitor of claim 21, wherein at least two of the first, second, and third annular regions are disposed at different heights.

30. The menstrual cycle monitor of claim 20, wherein the ordered set is disposed clockwise on the second annular region beginning with the initial indicator.

31. The menstrual cycle monitor of claim 20, wherein the marker comprises an arrow and the indicators of the ordered set comprise dots.

32. The menstrual cycle monitor of claim 20, wherein:
the first indicia comprises a first color, the second indicia comprises a second color, the third indicia comprises a third color, with the first, second, and third colors being different from each other, and
the indicia of the twenty-seventh indicator comprises a fourth color, the indicia of the other indicators in the fourth set comprises the second color, with the fourth color being different from the second color.

33. The menstrual cycle monitor of claim 1, further comprising:
a first region with a marker disposed thereon; and
a second region with the ordered set disposed thereon,
wherein at least one of the first and second regions is annular and rotatable with respect to the other, and the indicators of the ordered set are indexed with the marker so that the marker is alignable with each indicator at rotatable indexed positions.

34. The menstrual cycle monitor of claim 33, wherein the first and second regions are annular and concentric about a central axis.

35. The menstrual cycle monitor of claim 34, wherein the first and second regions are generally disposed in the same plane.

36. The menstrual cycle monitor of claim 34, further comprising a central display region for indicating time.

37. The menstrual cycle monitor of claim 36, further comprising a watch band or bracelet.

38. The menstrual cycle monitor of claim 33, wherein the at least one of the first and second regions is unidirectionally rotatable in clockwise or counterclockwise fashion and releasably lockable in the rotatable indexed positions.

39. The menstrual cycle monitor of claim 38, wherein the first region has an inner diameter and the second region has an outer diameter, the outer diameter being about the same as or smaller than the inner diameter so that the first region is rotatable about an edge of the second region defined at the outer diameter.

40. The menstrual cycle monitor of claim 39, further comprising a central display region for indicating time, wherein the second region is fixed in location with respect to the central display region.

41. The menstrual cycle monitor of claim 33, wherein at least one of the first and second regions is manually rotatable with respect to the other.

42. The menstrual cycle monitor of claim 33, wherein at least one of the first and second regions is automatically rotatable with respect to the other.

43. The menstrual cycle monitor of claim 1, wherein the ordered set of indicators are displayed electronically.

44. The menstrual cycle monitor of claim 43, further comprising a marker.

45. The menstrual cycle monitor of claim 44, wherein the marker is displayed electronically.

46. The menstrual cycle monitor of claim 43, wherein the ordered set is graphically displayed on a computer monitor.

47. The menstrual cycle monitor of claim 43, wherein the ordered set is graphically displayed on the screen of a hand-held computer.

48. The menstrual cycle monitor of claim 43, wherein the ordered set is displayed via internet communications.

49. A method of monitoring the menstrual cycle of a human female comprising:

providing an initial indicator with first indicia representing a first day of menstrual bleeding;

providing a second set of indicators comprising six indicators disposed adjacent one another, each of the six indicators provided with second indicia representing early infertile days;

providing a third set of indicators comprising twelve indicators disposed adjacent one another, each of the twelve indicators provided with third indicia representing fertile days;

providing a fourth set of indicators disposed adjacent one another representing later infertile days;

ordering the indicators together to form an ordered set with the initial indicator disposed adjacent an indicator from the second set, the second set disposed between the initial indicator and the third set, the third set disposed between the second and fourth sets, and an indicator from the fourth set disposed adjacent an indicator from the third set, with the ordered set including a twenty-seventh indicator determined by counting each consecutive indicator starting with the initial indicator;

providing the twenty-seventh indicator with different indicia from indicia provided to the other indicators in the fourth set.

50. A method of assisting a human female to monitor her menstrual cycle, said female having an initial indicator representing a first day of menstrual bleeding, a second set of indicators consisting of six indicators representing early infertile days, a third set of indicators consisting of twelve indicators representing fertile days, and a fourth set of indicators representing later infertile days, the indicators forming an ordered set with the initial indicator disposed adjacent an indicator from the second set, the second set disposed between the initial indicator and the third set, the third set disposed between the second and fourth sets, the ordered set including a twenty-seventh indicator determined by counting each consecutive indicator starting with the initial indicator, and a movable marker for coupling to each indicator, the method comprising the steps of:

instructing the female to couple the movable marker to the initial indicator on the first day of menstrual bleeding at the beginning of her menstrual cycle;

instructing the female to advance and couple the movable marker to an adjacent indicator each day without advancing the movable marker to the same indicator more than once during her menstrual cycle;

instructing the female to consult her health care provider if menstrual bleeding occurs when the movable marker is coupled to one of the indicators in the third or fourth sets and prior to the twenty-seventh indicator.

51. The method of claim 50, further comprising:

instructing the female to consult her health care provider if menstrual bleeding occurs when the movable marker is coupled to one of the indicators in the fourth set after a thirty-second indicator determined by counting each consecutive indicator starting with the initial indicator.

52. The method of claim 50, further comprising:

instructing the female to avoid unprotected intercourse when the movable marker is coupled to one of the indicators in the third set.

53. The method of claim 51, further comprising:

instructing the female to avoid unprotected intercourse when the movable marker is coupled to one of the indicators in the third set.

54. A menstrual cycle monitor for a human female comprising:

an initial indicator provided with first indicia representing a first day of menstrual bleeding;

a second set of indicators consisting of six indicators disposed adjacent one another, each of the six indicators provided with second indicia representing early infertile days;

a third set of indicators consisting of twelve indicators disposed adjacent one another, each of the twelve indicators provided with third indicia representing fertile days; and a fourth set of indicators disposed adjacent one another representing later infertile days;

wherein the indicators together comprise an ordered set with the initial indicator disposed adjacent an indicator from the second set, the second set disposed between the initial indicator and the third set, the third set disposed between the second and fourth sets, and an indicator from the fourth set disposed adjacent an indicator from the third set, and the ordered set includes a twenty-seventh indicator determined by counting each consecutive indicator starting with the initial indicator, and the twenty-seventh indicator is provided with different indicia from indicia provided to the other indicators in the fourth set.

55. The menstrual cycle monitor of claim 54, wherein the fourth set of indicators consists of thirteen indicators.

56. The menstrual cycle monitor of claim 54, wherein the ordered set of indicators are coupled together.

57. The menstrual cycle monitor of claim 54, wherein the ordered set includes a thirty-second indicator determined by counting each consecutive indicator starting with the initial indicator, the indicators of the ordered set being coupled together.

58. The menstrual cycle monitor of claim 54, further comprising a movable marker for placement around an indicator.

59. The menstrual cycle monitor of claim 54, wherein the indicia of the twenty-seventh indicator comprises a first shape, the indicia of the other indicators in the fourth set comprises a second shape, and the first shape is different from the second shape.

* * * * *